United States Patent [19]

Bohn et al.

[11] 4,254,021

[45] Mar. 3, 1981

[54] TISSUE SPECIFIC PROTEIN AND PROCESS FOR PREPARING SAME

[75] Inventors: Hans Bohn, Marburg an der Lahn; Wilhelm Winckler, Wenkbach, both of Fed. Rep. of Germany

[73] Assignee: Behringwerke Aktiengesellschaft, Marburg an der Lahn, Fed. Rep. of Germany

[21] Appl. No.: 68,459

[22] Filed: Aug. 21, 1979

Related U.S. Application Data

[63] Continuation-in-part of Ser. No. 830,775, Sep. 6, 1977, abandoned.

[30] Foreign Application Priority Data

Sep. 8, 1976 [DE] Fed. Rep. of Germany ....... 2640387

[51] Int. Cl.³ .................. A61K 35/50; A61K 39/395; C07G 7/00
[52] U.S. Cl. .............. 260/112 B; 260/112 R; 424/85; 424/88; 424/95; 424/101; 424/105; 424/177
[58] Field of Search ...... 260/112 R, 112 B; 424/101, 105, 88, 85, 95, 177

[56] References Cited

U.S. PATENT DOCUMENTS

| | | | |
|---|---|---|---|
| 3,409,605 | 11/1968 | Florini | 260/112 R |
| 3,497,492 | 2/1970 | Buck et al. | 424/105 |
| 3,904,751 | 9/1975 | Zwisler et al. | 424/105 |
| 3,910,822 | 10/1975 | Pentchev et al. | 424/105 |
| 3,931,399 | 1/1976 | Bohn et al. | 424/105 |
| 4,018,885 | 4/1977 | Bohn et al. | 260/112 R |
| 4,041,021 | 8/1977 | Bohn | 260/112 B |
| 4,191,533 | 3/1980 | Bohn et al. | 260/112 B |

OTHER PUBLICATIONS

Centonze et al., *Chemical Absts.*, vol. 51:16,804e (1957).
Centonze et al., *Chemical Absts.*, vol. 55:23,724f (1961).
Bohn et al., *Chemical Absts.*, vol. 77:118,184f (1972).
Mansfield et al., *Chemical Absts.*, vol. 65:9157a (1963).
Bohn et al., *Chemical Absts.*, vol. 76:70,559g (1972).
Bohn, *Chemical Absts.*, vol. 77:162,901m (1972).
Bohn, *Chemical Absts.*, vol. 83:92,637c (1975).
Bohn, *Chemical Absts.*, vol. 76:32,096w (1972).

*Primary Examiner*—Howard E. Schain
*Attorney, Agent, or Firm*—Curtis, Morris & Safford

[57] ABSTRACT

The invention relates to a tissue specific protein, i.e. a substance which is a constituent of parenchymatous tissues, and to a process for preparing the same. The tissue protein is characterized by a protein proportion of 94±3%, essentially consisting of α-amino acids, an amino acid analysis of

| | Mol % | Variation coefficient (%) |
|---|---|---|
| lysine | 5,64 | 12.7 |
| histidine | 1.05 | 15.0 |
| arginine | 3.83 | 9.2 |
| aspartic acid | 9.84 | 6.8 |
| threonine | 4.33 | 15.7 |
| serine | 4.78 | 8.2 |
| glutamic acid | 11.29 | 3.5 |
| proline | 6.41 | 9.2 |
| glycine | 8.65 | 9.8 |
| alanine | 7.51 | 6.4 |
| cystine/2 | 2.11 | 12.6 |
| valine | 6.68 | 7.9 |
| methionine | 0.98 | 14.5 |
| isoleucine | 3.32 | 7.4 |
| leucine | 14.43 | 4.2 |
| tyrosine | 5.10 | 14.9 |
| phenylalanine | 3.08 | 13.5 |
| and tryptophan | 1.14 | 11.4 | a carbohydrate proportion of 5.4±2.2% consisting of 3.0±1% of hexoses, 1.2±0.5% of hexosamine, 0.2±0.2% of fucose, and 1.0±0.5% of neuraminic acid, a sedimentation coefficient $S_{20,w}^{c=0.1}$ of 3.5 S±0.5 S, a molecular weight determined by the sedimentation equilibrium method of 37,100+1,400, an isoelectric point of 4.9±0.3, measured with polyamide gel plates and of 4.5±0.3, measured in an electrofocussing column, an electrophoretic mobility in the range between the $\alpha_2$- and $\beta_1$-globulins, an extinction coefficient $E_{1\ cm}^{1\%}$ (278 nm) of 11.9±1.0, and a specific immunologic reaction with an antibody specifically directed against the protein.

3 Claims, No Drawings

TISSUE SPECIFIC PROTEIN AND PROCESS FOR PREPARING SAME

This is a continuation-in-part-application of our application Ser. No. 830,775 filed Sept. 6, 1977, now abandoned.

This invention relates to a tissue specific protein, i.e. a substance which is a constituent of parenchymatous tissues, and to a process for preparing the same.

Several, already described, substances can be isolated in a relatively pure form from disintegrated organs of mammals. There is known, for example, the iron-containing protein ferritin, which can be prepared from placental tissue and which has been detected also in the stomach, spleen, liver, kidney, uterus and lung.

It is the object of the present invention to provide a novel tissue protein which is characterized by a protein proportion of 94±3%, essentially consisting of α-amino acids,
an amino acid analysis of

|  | Mol % | Variation coefficient (%) |
|---|---|---|
| lysine | 5,64 | 12.7 |
| histidine | 1.05 | 15.0 |
| arginine | 3.83 | 9.2 |
| aspartic acid | 9.84 | 6.8 |
| threonine | 4.33 | 15.7 |
| serine | 4.78 | 8.2 |
| glutamic acid | 11.29 | 3.5 |
| proline | 6.41 | 9.2 |
| glycine | 8.65 | 9.8 |
| alanine | 7.51 | 6.4 |
| cystine/2 | 2.11 | 12.6 |
| valine | 6.68 | 7.9 |
| methionine | 0.98 | 14.5 |
| isoleucine | 3.32 | 7.4 |
| leucine | 14.43 | 4.2 |
| tyrosine | 5.10 | 14.9 |
| phenylalanine | 3.08 | 13.5 |
| and tryptophan | 1.14 | 11.4 | a carbohydrate proportion of 5.4±2.2% consisting of 3.0±1% of hexoses, 1.2±0.5% of hexosamine, 0.2±0.2% of fucose and, 1.0±0.5% of neuraminic acid,
a sedimentation coefficient $S_{20,w}^{c=0.1}$ of 3.5±0.5 S,
a molecular weight determined by the sedimentation equilibrium method of 37,100±1,400,
an isoelectric point of 4.9±0.3, measured with polyamide gel plates and of 4.5±0.3, measured in an electrofocussing column, an electrophoretic mobility in the range between the $\alpha_2$- and $\beta_1$-globulins,
an extinction coefficient $E_{1\ cm}^{1\%}$ (278 nm) of 11.9±1.0, and a specific immunologic reaction with an antibody specifically directed against the protein.

It is a special characteristic of the novel tissue protein that it can be detected in fetal organs as well as in adult organs of mammals. In primates, and especially in men, the protein has been identified in the following fetal organs: heart, liver, kidney, lung, stomach, cerebrum, and in the following adult organs; heart, lung, skin, stomach, kidney, uterus, liver, spleen, suprarenal gland, colon, rectum, and bladder. In general, at least 10 mg of the protein can be detected in 100 g of tissue by quantitative immunologic methods. The product is also contained in the placenta in an amount of 10 mg per 100 g of tissue. For the isolation of the protein, the placenta is especially suitable. In erythrocytes 1 mg of the protein can be detected in 100 ml of erythrocytes, whereas in the plasma or serum of healthy individuals the protein cannot be detected.

To define the characteristic features of the protein the following methods were used:

The sedimentation coefficient was determined in an analytic ultra-centrifuge at 60,000 revolutions per minute in double sector cells with the aid of the migrating bands of the substance in the ultraviolet range at a wave length of 280 nm using water as solvent and a protein concentration of 1 mg/ml in a layering cell of an analytical ultra-centrifuge analogous to the method described by Vinograd inProc. Acad. Sci. USA, 49, 902 (1963)

The molecular weight was calculated, on the one hand, by determining the sedimentation equilibrium according to Yphantis. A value of 37,100±1,400 was found.

On the other hand, by analyzing the protein in a carrier gel consisting of polyacryl amide and containing 0.1% of sodium dodecyl sulfate, the major proportion of the protein was decomposed into 2 sub-units having a molecular weight of 22,000±2,000, from which a molecular weight of 44,000±4,000 could be derived for the native protein.

To determine the isoelectric point, the process of isoelectric focussing was used in the apparatus and with the reagents sold by Messrs. LKB, Stockholm, Sweden.

Using polyamide gel plates of Messrs. LKB, an isoelectric point of 4.9±0.3 was found, whereas electrofocussing in a column of the same firm with the recommended reagents indicated an isoelectric point of 4.5±0.3 for the protein of the invention.

The electrophoretic mobility of the protein was determined with the use of cellulose acetate as a carrier film.

The carbohydrates were determined according to H. E. Schultze, R. Schmidtberger, H. Haupt "Untersuchungen über die gebundenen Kohlenhydrate in isolierten Plasmaproteinen" Biochem. Z., 329, page 490 (1958).

The amino acid analysis was carried out according to S. Moore, D. H. Spackman, W. H. Stein "Chromatography of amino acids on sulfonated polystyrene resins" Anal. Chem. 30, page 1185 (1958) with the use of liquid chromatography. It was found that leucine, glutamic acid, aspartic acid and glycine were the most frequently occurring amino acids in the peptide chain.

The most simple way for an immunological characterization of the substance is a known diffusion process wherein an antigen, i.e. the protein, and an antibody, directed against the protein, or the antiserum without enriched antibody diffuse towards each other in a carrier medium, for example agar. When the two reaction components meet each other in a favorable ratio, a visible precipitate is formed. With this knowledge, it is obvious to the exerpt that all immunologic techniques for the detection and determination of the novel tissue protein and of the antibodies directed against said tissue protein can be used.

It is another object of the invention to provide processes for the preparation of the aforesaid protein, which processes comprise fractionating organ extracts, generally aqueous extracts of organs containing the said protein, with consideration of the following criteria.

The protein can be precipitated with neutral salts. With ammonium sulfate, which is generally used for precipitations of this kind, the protein can be precipitated, with a saturation concentration of the salt of from 30 to 60%, in a pH range near the neutral point.

According to its molecular weight, the protein can be isolated by measures suitable for separating substances having a molecular weight in the range of from 35,000 to 50,000, preferably by gel filtration of ultrafiltration.

At a neutral or weakly alkaline pH, the tissue protein can be adsorbed on weakly basic ion exchangers. In this process a relatively weakly concentrated buffer solution is used because an increase of the salt concentration or a reduction of the pH value can prevent adsorption. On the other hand, this behavior makes it possible first to adsorb the tissue protein and then to elute it again with the use of higher concentrated salt solutions of buffer solutions with reduced pH.

It has been found that the tissue protein cannot be precipitated with water-soluble organic bases of the acridine and quinoline series as generally used in precipitation processes. With the concentrations generally used in these processes, the protein remains in the aqueous supernatant. Hence, it is possible to use an acridine base, for example 2-ethoxy-6,9-diamino-acridine lactate, or a quinoline base, for example bis(2-methyl-4-aminoquinolyl-6)-carbamide hydrochloride, for precipitating accompanying proteins, while the tissue protein of the invention remains in the supernatant.

Similar considerations are valid for the use of hydroxyl apatite as an adsorbent for proteins. The tissue protein of the invention does not show a specific affinity for hydroxyl apatite, whereas a series of accompanying proteins are held back by hydroxyl apatite.

Having knowledge of the electrophoretic mobility, preparative zone electrophoresis can be used for the concentration or isolation of the tissue protein.

The affinity of the tissue protein as a result of its immunological behavior can be utilized to concentrate the protein with the aid of so-called immuno-adsorption processes. To this end, an immuno adsorbent, i.e. an antibody for the tissue protein bound to a carrier, can be prepared which specifically adsorbs the tissue protein. The protein can then be eluted again by changing the medium conditions.

By a selected combination of the aforesaid methods, which are suitable, on the one hand, to concentrate the tissue protein and, on the other, to separate it from the other accompanying substances, it is possible to isolate the protein of the invention. One of the objects of the present invention is, therefore, a combination of individual concentrating steps and processes for the purification of the tissue protein.

The process for concentrating the tisue protein comprises at least one of the following treatments of organ extracts or solutions obtained therefrom and containing the tissue protein and the subsequent isolation of the fraction enriched with tissue protein:

(a) Addition of water-soluble derivatives of an acridine or quinoline base, preferably 2-ethoxy-6,9-diamino-acridine lactate, in a pH range of from 5 to 10, preferably about 8, to a final concentration of about 0.8% (weight to volume), whereby the tissue protein substantially remains in the supernatant.

(b) Addition to neutral salts until the tissue protein is precipitated, preferably ammonium sulfate at an approximately neutral pH, until 30 to 60% of the saturation concentration of ammonium sulfate has been reached.

(c) Adsorption of the tissue protein on a weakly basic ion exchanger, for example diethylaminoethyl cellulose at a conductivity of the solution of 0 to 2 mS and with a neutral or weakly alkaline pH, for example by using about 0.01 molar buffer of a pH of about 8, preferably tris-hydroxymethylaminoethane—HCl, with subsequent elution of the tissue protein by shifting the pH to a value below 7.0 or by increasing the conductivity to a value above 5 mS.

(d) Separation on the basis of the molecular size (molecular sieve fractionation), preferably by gel filtration in a column filled with a polymer having an appropriate pore size, for example dextran cross-linked with epichlorohydrin, prepared and sold under the name of SEPHADEX ® by Messrs. Pharmacia, Uppsala, whereby proteins having a molecular weight of about 50,000 are concentrated; products such as ULTROGEL ® by LKB, Bromma or BIO-Gel P ® by Bio-rad Laboratories, Richmond, Calif. being likewise suitable.

(e) Adsorption with hydroxyl apatite. Under the conditions generally maintained in preparative biochemistry, the tissue protein is not adsorbed by hydroxyl apatite and, therefore, this substance is a suitable reagent to remove accompanying tissue proteins from solution. The adsorption is suitably carried out at a pH near the neutral point of the solution and the conductivity of the solution is maintained at about 1 mS.

(f) Preparative zone electrophoresis. A solution containing the protein and suitable for an electrophoresis of protein, preferably an alkaline buffer solution such as a sodium diethyl barbiturate buffer of pH 8.6, ion strength 0.1, is introduced into an apparatus for preparative electrophoresis, for example as described by N. Heimburger and R. Schmidtberger in "Behringwerke-Mitteilungen," number 43, pages 83 et seq, more particularly pages 119 to 120, comprising a horizontal open trough in which electrophoresis is carried out on a carrier material. To dissipate the Joule's heat generated in the electrophoresis, the carrier material is cooled to a temperature below 10° C. As carrier material, substances which are inert towards proteins are used, preferably polyvinyl chloride or copolymers of vinyl chloride in the form of fine granules.

It proved advantageous to carry out the electrophoresis in the alkaline pH range, preferably at about pH 8.6, at an ion strength of from 0.08 to 0.12 and a field intensity of 4 to 6 volts per cm. Using 0.1 molar sodium diethyl barbiturate buffer of pH 8.6, the tissue protein migrates in the electrical field into the region of the plasma proteins classified as $\alpha_2$ and $\beta_1$ zones.

To obtain the high molecular weight $\alpha$-globulins, this zone is cut out and the desired substance is removed from the inert carrier material by elution with water or aqueous salt solutions, for example sodium chloride solution of 0.5 to 1% strength. In a last purification step, the eluate can be subjected to a gel filtrate, preferably after having been concentrated on an ultrafilter.

For the preparation of the novel tissue protein, several of the aforesaid measures can be combined and, after each step, the fraction containing the tissue is further treated while the remaining fractions are rejected.

Without constituting any limitation, the following description illustrates, by way of example, a possible mode of preparation of the tissue protein from parenchymatous tissue.

Human placentae are comminuted and extracted with water or a dilute salt solution of less than 10% strength, preferably a 0.5% neutral salt solution, for example of sodium chloride. About 1 to 5 liters of extraction solution are preferably used for 1 kg of placenta. The undissolved portions are separated from the extract by centrifugation or filtration.

It proved advantageous to isolate the tissue protein at a temperature below room temperature, for example 10° C. To the neutral or weakly alkaline placental extract, which is preferably adjusted to a pH of about 8, there is then added a water-soluble derivative of an acridine base, for example 2-ethoxy-6,9-diamino-acridine lactate up to a concentration of $0.8 \pm 0.4\%$, or a water-soluble derivative of a quinoline base, preferably bis(2-methyl-4-aminoquinolyl-6)-carbamide hydrochloride, up to a concentration of $0.3 \pm 0.15\%$. The precipitate formed is rejected. The supernatant contains the major proportion of the tissue protein to be concentrated. The precipitating agent in excess is expediently separated by adding compounds which form a precipitate therewith. The acridine bases, for example, form difficulty soluble compounds with halides so that the addition of sodium chloride offers itself for separating the acridine base. A satisfactory separation is achieved with a concentration of about 3 to 7% (wt/v) of sodium chloride. The supernatant protein solution is then admixed with a salt suitable for the precipitation of proteins in an amount such that the tissue protein is caused to precipitate. To this end, ammonium sulfate is preferably used in an amount to maintain a saturation concentration of said salt of 40 to 60%, preferably 40 to 50%. The precipitate formed after the addition of ammonium sulfate is separated by centrifugation or filtration and then redissolved in water. Generally, precipitates of this type obtained by salt precipitation include residues of the precipitating agent and, therefore, it is recommended to perform a dialysis thereafter. The protein solution is dialyzed suitably against a little concentrated buffer solution, for example as used in ion exchange chromatography, which makes possible an adsorption of the tissue protein on a weakly basic ion exchanger.

The dialyzed solution of the tissue protein is then mixed, in a weakly concentrated buffer medium, with a weakly basic ion exchanger, for example diethylaminoethyl cellulose and, after adsorption of the tissue protein on the ion exchanger, the latter is separated from the remaining solution, for example by filtration. If the adsorption is carried out in a weakly alkaline medium (about pH 8.0) with a buffer having a concentration of approximately 0.01 mol per liter, the ion exchanger can be washed with a 0.02 molar buffer of slightly reduced pH (about 6-7). The elution buffer may have a total salt concentration of about 0.2 mol per liter.

It is advantageous to add to the eluate an amount of neutral salt sufficient to precipitate the protein in the dilute solution. By dissolving the precipitate the protein is then obtained in concentrated form. For further purification the dissolved protein can then be subjected to a gel filtration. Fractions highly enriched with the desired tissue protein are obtained by using for the gel filtration a three-dimensionally cross-linked dextran of Messrs. Pharmacia known by the name of SEPHADEX®, Type G 150, preferably in column chromatography. For the elution buffer, solutions common in biochemistry can be used, to which neutral salts can be added to improve the fractionating effect, for example 0.01 to 0.1 mol of tris-hydroxymethylaminomethane hydrochloric acid buffer with an addition of 0 to 5 mols of NaCl, which solutions have an approximately neutral to basic pH. In this elution process the eluted fractions are analyzed, preferably by immunological methods, to find the tissue protein and the fractions containing the same are separated and collected.

The eluates resulting from gel filtration also contain the tissue protein in dilute form and, therefore, a concentration by precipitation with neutral salts as described above can be performed.

The solution of the tissue protein obtained by re-dissolution of the salt precipitate is dialyzed against a strongly diluted buffer solution and thereby adjusted to conditions which permit adsorbing on hydroxyl apatite as many as possible of the impurities still present. Weakly concentrated phosphate buffers, for example about 0.005 molar sodium phosphate buffer having a pH in the range of from about 6.5 to 7.0 are especially suitable. When the protein solution comes into contact with the hydroxyl apatite, the tissue protein of the invention substantially remains in solution. Hence, in the following process step the hydroxyl apatite, which is preferably in a column, need not be considered any more. The solution passed through the hydroxyl apatite column contains the desired tissue protein in further enriched and purified form.

For further concentration of the tissue protein, the ion exchange chromatography can be repeated. However, at variance with the steps described above, the ion exchanger is introduced into a column, the solution containing the tisssue protein is charged to the column, and the column is eluted with a salt solution of increasing gradient. The process steps listed above by way of example yield the tissue protein with a purity of over 99%.

It is also possible, of course, to obtain the tissue protein with the same degree of purity by combining different measures, for example by inserting additionally a preparative electrophoresis or an immuno adsorption.

The tissue protein prepared according to the invention has antigenic properties. An immunization of animals performed therewith according to known methods leads to the formation of specific antibodies in the blood of the immunized animals. Sera can be obtained therefrom by usual methods and enriched with the antibodies contained therein.

Owing to its tissue specificity, the substance of the invention can be used in diagnostics. Tissue diseases can be detected by the migration of the protein from the tissue into the blood stream. To this effect, essentially the known immunological modes of detection using the specific antibodies for the tissue protein may be used.

The following example illustrates the invention.

EXAMPLE 150 kg of deep-frozen placentas were comminuted and extracted with 150 l of a 0.5% aqueous sodium chloride solution. The extract was adjusted to pH 8 with 2 N sodium hydroxide solution and 50 l of a 3% aqueous solution of diaminoethoxyacridine lactate were added. After a waiting period of 1 hour, the supernatant, which contained the tissue protein, was siphoned off, 5% of solid sodium chloride (11 kg) were added to precipitate the dissolved diaminoethoxyacridine lactate, the mixture was filtered, 30%, calculated on the weight of the liquid, of solid ammonium sulfate were added and the liquid was thoroughly stirred. After 1 hour, the precipitate was filtered off.

500 g of the precipitate collected on the filter were dissolved in 500 ml of distilled water and dialyzed against a 0.01 molar tris (hydroxymethyl)-aminomethane hydrochloric acid buffer solution of pH 7.0 containing 0.05% of sodium azide. The dialyzed solution was centrifuged and the supernatant was made up to 2,000 ml with the same buffer solution, adjusted to pH 8.0 with 0.1 N sodium hydroxide solution and stirred for 1 hour with 500 g moist diethylaminoethyl cellulose (Messrs. Serva, Heidelberg).

The diethylaminoethyl cellulose was separated from the solution by filtration, washed twice, each time with 1 liter of 0.01 molar tris(hydroxymethyl)-aminomethane-hydrochloric acid buffer of pH 8.0, and then eluted three times, each time with 500 ml of 0.02 molar tris(hydroxymethyl)-aminomethane-hydrochloric acid buffer of pH 6.5 containing 0.85% of sodium chloride and 0.05% of sodium azide.

Next, 30% of ammonium sulfate, calculated on the liquid weight, were added to the combined eluates and the whole was stirred. The precipitate containing the tissue protein was separated and dissolved in 300 ml of distilled water and subjected to gel filtration with SEPHADEX ® G-150 using 0.1 molar tris-(hydroxymethyl)-aminomethane-hydrochloric acid buffer of pH 8.0 containing 1.0 mol of sodium chloride per liter (100:20 cm column). In the gel filtration the tris buffer was used as a suspension medium for the carrier for the gel filtration, i.e. SEPHADEX ® G-150 and as eluting agent for the tissue protein dissolved in distilled water and charged to the column filled with SEPHADEX ®.

The eluates were analyzed with specific antiserum for the tissue protein, the fractions containing the tissue protein were collected and the proteins precipitated again as described above with 30% solid ammonium sulfate.

For further purification, hydroxyl apatite (column 3×23 cm) and a 0.005 molar phosphate buffer of pH 6.8 were used and then chromatography on diethylaminoethyl-SEPHADEX ® (Pharmacia) (column 3×23 cm) using a tris-HCl buffer of pH 7.0 was performed. For the elution a salt gradient of 0 to 2% NaCl was used. 40 mg of the novel tissue protein were obtained having a purity of 99.5%.

| | Mol % | Variation coefficient (%) |
|---|---|---|
| lysine | 5,64 | 12.7 |
| histidine | 1.05 | 15.0 |
| arginine | 3.83 | 9.2 |
| aspartic acid | 9.84 | 6.8 |
| threonine | 4.33 | 15.7 |
| serine | 4.78 | 8.2 |
| glutamic acid | 11.29 | 3.5 |
| proline | 6.41 | 9.2 |
| glycine | 8.65 | 9.8 |
| alanine | 7.51 | 6.4 |
| cystine/2 | 2.11 | 12.6 |
| valine | 6.68 | 7.9 |
| methionine | 0.98 | 14.5 |
| isoleucine | 3.32 | 7.4 |
| leucine | 14.43 | 4.2 |
| tyrosine | 5.10 | 14.9 |
| phenylalanine | 3.08 | 13.5 |
| and tryptophan | 1.14 | 11.4 |

What is claimed is:

1. An isolated, concentrated tissue protein obtained by fractionating an organ extract or a solution obtained from such an extract, said tissue protein having:
   (a) a protein proportion of 94±3%;
   (b) an amino acid analysis of

| | Mol % | Variation coefficient (%) |
|---|---|---|
| lysine | 5,64 | 12.7 |
| histidine | 1.05 | 15.0 |
| arginine | 3.83 | 9.2 |
| aspartic acid | 9.84 | 6.8 |
| threonine | 4.33 | 15.7 |
| serine | 4.78 | 8.2 |
| glutamic acid | 11.29 | 3.5 |
| proline | 6.41 | 9.2 |
| glycine | 8.65 | 9.8 |
| alanine | 7.51 | 6.4 |
| cystine/2 | 2.11 | 12.6 |
| valine | 6.68 | 7.9 |
| methionine | 0.98 | 14.5 |
| isoleucine | 3.32 | 7.4 |
| leucine | 14.43 | 4.2 |
| tyrosine | 5.10 | 14.9 |
| phenylalanine | 3.08 | 13.5 |
| and tryptophan | 1.14 | 11.4 |

(c) a carbohydrate proportion of 5.4±2.2% consisting of 3.0±1% of hexoses, 1.2±0.5% of hexosamine, 0.2±0.2% of fucose, and 1.0±0.5% of neuraminic acid.
   (d) a sedimentation coefficient $S_{20,w}{}^c{}^{=0.1}$ of 3.5 S±0.5 S;
   (e) a molecular weight determined by the sedimentation equilibrium method of 37,100±1,400;
   (f) an isoelectric point of 4.9±0.3, measured with polyamide gel plates, and of 4.5±0.3, measured in an electrofocussing column, an electrophoretic mobility in the range between the $\alpha_2$- and $\beta_1$-globulins; and
   (g) an extinction coefficient $E_1\ {}_{cm}{}^{1\%}$ (278 nm) of 11.9±1.0.

2. A tissue protein as in claim 1 obtained by fractionating an extract of human placentas.

3. An antiserum to the tissue protein of claim 1 obtained by injecting said tissue protein into an animal, taking the blood of the animal after some time, and recovering the serum from said blood.

* * * * *